United States Patent
Weidman et al.

[11] Patent Number: 6,009,971
[45] Date of Patent: Jan. 4, 2000

[54] SELF-ADHERENT DISPOSABLE STETHOSCOPE SHIELD SYSTEM

[76] Inventors: Richard C. Weidman, 9505 Neuse Way, Great Falls, Va. 22066; W. Jeffrey Weidman, 2187 Greenkeepers Ct., Reston, Va. 20191

[21] Appl. No.: 09/081,679

[22] Filed: May 20, 1998

[51] Int. Cl.$^7$ ........................................................ A61B 7/02
[52] U.S. Cl. ............................................ 181/131; 181/137
[58] Field of Search ..................................... 181/131, 137

[56] References Cited

U.S. PATENT DOCUMENTS

| | | |
|---|---|---|
| 4,867,268 | 9/1989 | Ulert ........................................ 181/137 |
| 4,871,046 | 10/1989 | Turner . |
| 5,424,495 | 6/1995 | Wurzburger . |
| 5,448,025 | 9/1995 | Stark et al. . |
| 5,528,004 | 6/1996 | Wurzburger . |
| 5,587,561 | 12/1996 | Budayr et al. . |
| 5,686,706 | 11/1997 | Wurzburger . |
| 5,808,244 | 9/1998 | Knight et al. ............................ 181/131 |

OTHER PUBLICATIONS

Contaminated Stethoscopes Revisited, by Melinda A. Smith, MPH; John J. Mathewson, PhD; I. Alan Uler, MD; Ernesto G. Scerpella, MD; and Charles D. Ericsson, MD; Arch Intern Med/vol. 156, Jan. 8, 1996, pp. 82–84.

The Stethoscope A Potential Source of Nosocomial Infection?, by Mark A. Marinella, MD; Carl Pierson, PhD; and Carol Chenoweth, MD; Arch Intern Med/vol. 157, Apr. 14, 1997, pp. 786–790.

Graham–Field To Distribute Patented Stethoscope Cover; Scope Shield Protects Patients Against Infectious Diseases, Graham–Field Health Products, Inc., Feb. 18, 1998.

*Primary Examiner*—Khanh Dang
*Attorney, Agent, or Firm*—Sixbey, Friedman, Leedom & Ferguson, P.C.; Donald R. Studebaker

[57] ABSTRACT

A stethoscope shield unit comprising a plurality of substantially planar shield stacked one upon the other, each of the shields including a first surface having an adhesive applied thereto and a second surface such that adjacent shields adhere to one another with the first surface of each of these shields adhering to the second surface of an adjacent shield with a first shield of the plurality of shields being adhered to the diaphragm of the stethoscope for supporting the plurality of shields wherein an exposed shield of the plurality of shields is removed after contacting the body of a patient. A protective shield devoid of an adhesive may be positioned adjacent the first shield of the plurality of shields with the protective shield being removed prior to adhering the first shield of the stack to the diaphragm. A method for preventing contamination of an instrument, particularly a stethoscope includes the steps of applying a plurality of substantially planar shields stacked one upon another to the surface of the stethoscope, each of the shields including a first surface having an adhesive applied thereto and a second surface such that adjacent shields adhere to one another with the first surface of each of the shields being adhered to the second surface of an adjacent shield and the first surface of a first shield in the stack adjacent the surface is adhered to the surface and subsequently removing an outermost shield of the stack after application of the instrument to each sequential patient.

34 Claims, 2 Drawing Sheets

SELF-ADHERENT DISPOSABLE STETHOSCOPE SHIELD SYSTEM

TECHNICAL FIELD OF THE INVENTION

The present invention is directed to a method of shielding a stethoscope to prevent the transmission of disease between patients and more particularly to a shielding system which attaches to the stethoscope head prior to an initial use which shields subsequently being removed to prevent the disease transmission between patients on which the stethoscope is being used.

BACKGROUND OF THE INVENTION

The use of stethoscopes is wide-spread in the medical community. With the increasing incidence of hospital acquired infections estimated by the CDC to be 2.4 million cases causing 100,000 deaths per year and with the recent emergence of multiple-antibiotic resistant organisms, particularly vancomycin-resistant staphylococci and other bacteria for which no current antibiotics may be effective, techniques to minimize the spread of infection between patients have become vital.

The stethoscope typically includes a head portion with a diaphragm disposed thereon which is placed against the patient, and a pair of ear pieces in communication with the diaphragm through which the internal sounds of the human body can be heard. A health care provider places the ear pieces in his or her ears while applying the diaphragm against the skin of the patient. Due to the sensitivity of the diaphragm, the health care provider is able to hear inside of the patient's body and thereby diagnose illness or determine that no illness is present. For example, when the diaphragm is placed on the patient's chest, the health care provider can listen to the respiratory and heart sounds to determine whether abnormalities are present.

Unfortunately, by contacting the patient's skin, the stethoscope can become contaminated with microorganisms which might be present on the patient. This is especially significant with patients who have skin contaminated with dangerous infectious organisms which can be transmitted by skin contact. Using the same stethoscope on more than one patient progressively increases the risk that infectious diseases will be passed between patients. Although sterilization of the stethoscope would prevent most of the transferred disease, it is extremely impractical to sterilize a stethoscope between each use on a patient. For physicians, nurses and other health care professionals working in hospitals and other health care settings where numerous patients are examined in rapid succession, sterilization of the stethoscope would be next to impossible. Further, even the use of cleansing agents such as alcohol, which reduces but does not eliminate all microorganisms, is not practical in todays medical settings.

Because of these concerns, several means for reducing the spread of infectious diseases by way of a stethoscope have been developed. Particularly, several shields have been developed which fit over the stethoscope head. The shields typically include an elastic retention means to hold the shield on the stethoscope head when in use, and allow changing of the shield between each patient. Such shields, however, suffer from several problems. First, several of the shields are awkward to position on the stethoscope. Because many of the shields functionally require two hands to be used to place the shield over the head of the stethoscope, the health care provider must put down the patients charts, etc. in order to attach the shields. Further, the shields generally attach to the stethoscope's head by securing about the side opposite the diaphragm. In such a position, there is significant risk that air will be trapped between the diaphragm and the portion of the shield which will contact the patient. Those skilled in the art will appreciate that air adjacent the diaphragm greatly reduces the ability of the diaphragm to transmit the sounds within the patient's body. A shield of this type is illustrated in U.S. Pat. No. 4,871,046 issued to Turner.

U.S. Pat. Nos. 5,424,495, 5,528,004 and U.S. Pat. No. 5,686,706, each issued to Wurzberger disclose a dispensable, disposable cover for stethoscopes. The dispensable, disposable cover set forth therein prevents the transfer of disease or other contaminants through the incorporation of a shield having an adhesive backing for removably attaching the shield over the entire surface area of a diaphragm of the stethoscope. The shield is peelably detachable from the stethoscope diaphragm after use. In various embodiments of the cover set forth therein, the shield includes a pull-tab or flap which allows for the ease in manipulating the shield. However, these shields are individually dispensed from a dispenser by the health care professional and applied to the stethoscope individually. This requires the health care professional to come into unnecessary contact with the shield when applying the shield to the stethoscope. Moreover, this requires that a dispenser containing a supply of stethoscope shields be either carried by the health care professional or the need for a dispenser to be placed in not only each room but also corridors and waiting rooms within the medical facility. Moreover, should such dispenser not be readily available to the health care professional, the likelihood of such a shield being used is minimal.

Similarly, U.S. Pat. No. 5,448,025 issued to Stark et al. discloses a shield for temporary securement to a stethoscope head to completely cover a diaphragm of the stethoscope head and seal the interior and diaphragm from the ambient atmosphere. The cover includes a flat, double-sided thin plastic sheet and a layer of adhesive on one side of the sheet to releasably secure the cover to the outer rim surface of the stethoscope head. The shield is accommodated on a tape having a plurality of such shields thereon which is withdrawn from a dispenser, removed from the tape and applied to the stethoscope. Again, it is necessary for the health care professional to handle the shield and the dispenser in order to remove the shield from the tape and apply the shield to the stethoscope. Additionally, as discussed hereinabove, such a dispensing system requires that the health care professional carry a supply of the shields with them or that a dispensing mechanism be provided within each room of a medical facility. Clearly, there will be times when it is impractical to use the shield because such shield is not readily available to the health care professional.

A still further effort to overcome the aforementioned shortcomings, the stethoscope shield set forth in U.S. Pat. No. 5,587,561 issued to Budayr et al. includes an annular flange disposed to extend generally upwardly from the shield towards the head of the stethoscope to protect the stethoscope from body fluids disposed on those patient's skin. However, the shields are provided in a stack with the uppermost diaphragm being removed from the stack and applied to the stethoscope in the manner discussed hereinabove. Once again, such a system requires handling of the shield in some manner and likewise requires the medical care professional to carry a dispenser along with them or have a dispenser provided in each room of a medical facility which, as noted hereinabove, is not feasible. Additionally, this system requires the exposure of the adhesive to the environment over long periods of time and the use of two hands during application.

Clearly, there is a need for a stethoscope shield for protecting patients from transmission of diseases as well as a method of use of such shields which is practical to use in the environment to which it is intended. Further, there is a need for a stethoscope shield system which overcomes the above-noted deficiencies and which is of a design which may be implemented in rapid secession which is mandatory in a clinical setting and also provides an opportunity to monitor health care providers compliance with barrier protection polices of the medical facility.

SUMMARY OF THE INVENTION

The primary object of the present invention to overcome the aforementioned shortcomings associated with the prior art shields and dispensing methods.

Yet another object of the present invention is to provide a stethoscope shield as well as a method for use of such stethoscope shield for preventing the transmission of the diseases between patients.

A still further object of the present invention is to provide a stethoscope shield and method of using such shields which does not interfere with the function of the stethoscope.

A further object of the present invention is to provide a stethoscope shield and a method of using a plurality of such shields in a manner which is practical within a clinical setting.

An additional object of the present invention is to provide a method of applying a plurality of stethoscope shields which allows the medical care professional to ensure that such shields are used and that a new shield is exposed for each successive patient.

A still further object of the present invention is to provide a system wherein health care provider's compliance with barrier protection policies of a particular medical facility can be monitored and one which serves as a reminder to promote hand washing.

These, as well as additional objects of the present, are achieved by providing a stethoscope shield unit comprising a plurality of substantially planar shields stacked one upon the other, each of the shields including a first surface having an adhesive applied thereto and a second surface such that adjacent shields adhere to one another with the first surface of each of these shields adhering to the second surface of an adjacent shield with a first shield of the plurality of shields being adhered to the diaphragm of the stethoscope for supporting the plurality of shields wherein an exposed shield of the plurality of shields is removed after contacting the body of a patient. That is, because a stack of shields is initially applied to the stethoscope, the outermost or exposed shield may be readily removed by the medical care professional prior to contacting each successive patient. Moreover, this allows the used shield to be removed without physically contacting the underlying uncontaminated shield.

In addition to the foregoing, a protective shield devoid of an adhesive may be positioned adjacent the first shield of the plurality of shields with the protective shield being removed prior to adhering the first shield of the stack to the diaphragm. That is, a method for preventing microbial contamination of an instrument, particularly a stethoscope includes the steps of providing a surface of the instrument, applying a plurality of substantially planar shields stacked one upon another to the surface of the stethoscope, each of the shields including a first surface having an adhesive applied thereto and a second surface such that adjacent shields adhere to one another with the first surface of each of the shields being adhered to the second surface of an adjacent shield and the first surface of a first shield in the stack adjacent the surface is adhered to the surface and subsequently removing an outermost shield of the stack after the instrument has been used. Particularly, removing an outermost shield from a head of a stethoscope between application to each sequential patient. Further, the method may include the step of removing a protective shield from the initial shield to be adhered to the surface of the instrument prior to applying the plurality of shields to the surface of the instrument.

These, as well as additional objects and advantages of the present invention will become apparent from the following detailed description when read in light of the several figures.

DETAILED DESCRIPTION OF THE PRESENT INVENTION

Figure 1:
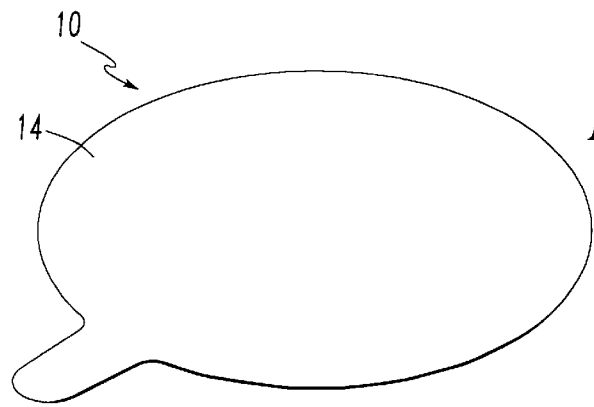
FIG. 1 is a perspective view of an individual shield for protecting a patient from the transmission of contaminants from an instrument, particularly a stethoscope in accordance with the present invention.

Reference will now be made to the several figures in which the various elements of the present invention will be discussed in detail. Like reference numerals will be utilized to designate like elements throughout the several figures.

With reference now to FIG. 1, there is shown a protective shield 10 for application to an instrument and particularly, application to the head of a stethoscope. The shield 10 includes a generally planar piece of sound transmissive material 14 wherein the sound transmissive material 14 may be of a variety of substances. However, it is preferred that the sound transmissive material 14 be of a thin sheet of plastic or paper or some other material which will not interfere with the transfer of sound between the patient and the diaphragm of the stethoscope. It is known that paper and plastic are commonly used materials in the health care profession and are advantageous in that they are both inexpensive and inherently disposable. In order to prevent body fluids from penetrating the shield, a shield made of paper would most likely include a thin fluid impermeable coating such as plastic or wax. In accordance with a preferred embodiment of the present invention, a thin essentially disc-shaped shield forms a waterproof and impermeable barrier to microorganisms for the stethoscope. As noted hereinabove, each of the disc-shaped shields 10 are disposable and are preferably constructed of a plastic polymeric material such as polyethylene having a thickness in the range of 0.01 to 4.0 mils.

Figure 1A:
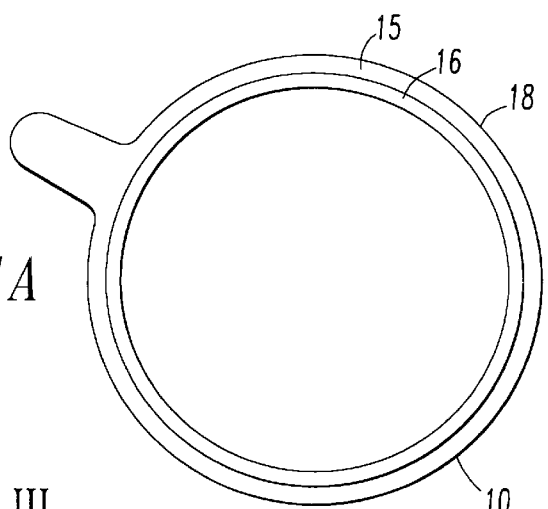
FIG. 1A is a plan view of the shield illustrated in FIG. 1.
Figure 2:
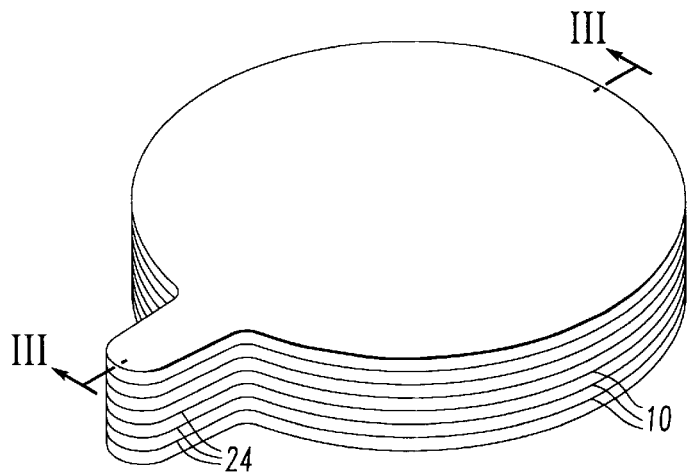
FIG. 2 is a perspective view of a stack of the shields illustrated in FIG. 1 for application to a head of a stethoscope in accordance with the present invention.

As can be seen from FIG. 2, the shield 10 is preferably provided in a stack of a plurality of such shields, stacked one upon the other. Applied to a first surface or underlying surface 15 of each of the shields 10 is an adhesive 16 which allows each sequential shield to be adhered to one another as well as an initial shield to be adhered to a surface of the stethoscope. This adhesive 16 which is preferably provided in the form of a annulus adjacent a periphery of the shield 10 is best illustrated in FIG. 1A. The adhesive utilized in accordance with the present invention is a removable adhesive, such as that used in note pads sold by 3M Corporation under the trademark "POST-IT NOTE". As such note pads have become extremely common, those skilled in the art will be familiar with numerous adhesives which will releasably hold the plurality of shields 10 to one another as well as the stack of shields to a surface of the stethoscope. While the adhesive 16 is illustrated as being in a annulus adjacent a periphery 18 of the shield 10, the adhesive 16 may cover a central region as well, however, for the reasons discussed in detail hereinbelow, the annulus of adhesive is preferred. Further, the adhesive of the initial shield contacting the instrument may be stronger than the adhesive between the remaining successive shields to aid in maintaining the stack secure with respect to the instrument as shields are removed.

Figure 3:
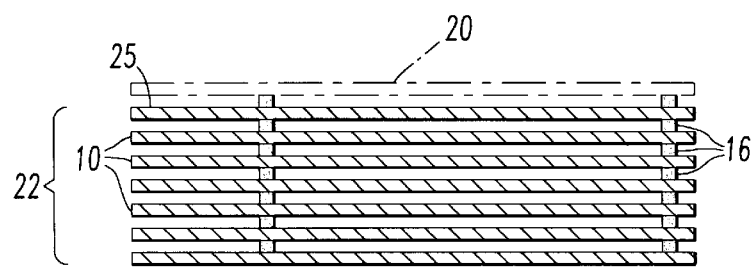
FIG. 3 is a cross-sectional view of the stack illustrated in FIG. 2 taken along line III—III of FIG. 2.

While FIG. 2 illustrates 5 shields 10 stacked one upon the other and FIG. 3 illustrates 7 shields stacked upon one another forming a unit 22, the actual number of shields forming the initial stack or unit which is applied to the stethoscope may vary and is clearly dependent upon the thickness and sound transmissibility of the material forming the shield. The thicker the material, the fewer number of shields are provided in the stack in order to ensure that the physician can adequately hear the sounds of the body during an exam. For this reason, as noted hereinabove, the adhesive 16 is provided about a periphery 18 of the shield 10 rather than covering the entire surface of the shield. By leaving the central region free of adhesive, sound transmission through the plurality of shields can be enhanced. However, if the thickness of the adhesive layer is minimized, the adhesive may be placed about an entire surface of the shield. FIG. 3 illustrates a plurality of shields 10 stacked one upon the other with the inclusion of a dummy shield or adhesiveness shield 20. This shield is removed from the stack prior to application to the stethoscope, the process of which will be described in greater detail hereinbelow. The dummy shield 20 acts to preserve the integrity of the uppermost adhesive ring 16 and aids in preventing contamination of the stack of shields 22. Preferably, the plurality of shields stacked one upon another are provided in a sealed pouch which maintains the sterility and integrity of the stack 22 when being handled. When used, the stack 22 is removed from the sterile pouch and the dummy shield 20 is removed so as to expose the uppermost adhesive ring 16 for application to a stethoscope. It is to be noted that the foregoing and following description is directed towards the use of a plurality of shields stacked one upon another in connection with a stethoscope. However, this concept is likewise applicable to any instrument wherein the need for maintaining a contaminant free surface is present. It should also be noted that each of the shields 10 includes a tab 24 extending from the periphery 18 of the shield 10. The particular importance of the tab will be described in greater detail hereinbelow with respect to the use of the stack of shields 22.

Figure 4:
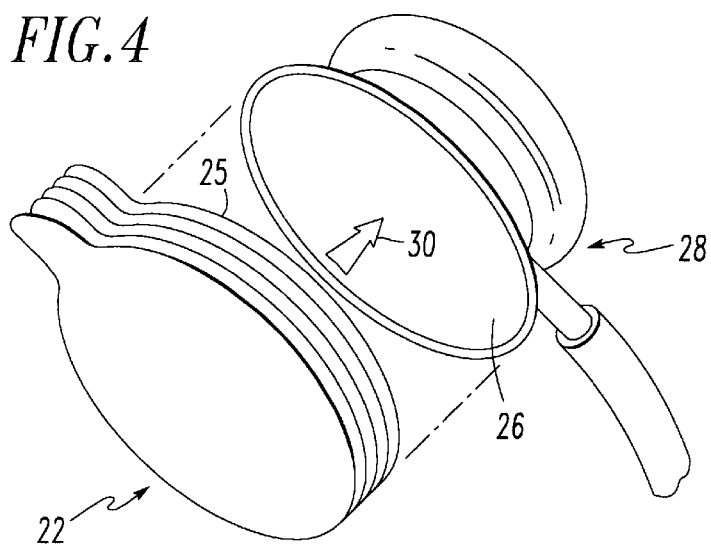
FIG. 4 is a perspective view of a stack of shields being applied to the head of a stethoscope in accordance with the present invention.

With reference now to FIG. 4, once the stack of shields 22 is removed from its packaging (not shown), the dummy shield 20 is removed from the placement shield 25 to expose the adhesive 16 of the initial shield in the stack. This stack is then secured to a diaphragm 26 of a stethoscope head 28. The stethoscope head may take on numerous configurations with the particular configuration of the adhesive 16 applied to the shield 10 being optimally suited for the particular stethoscope head. Once again, this concept may be applied to any instrument wherein it is desired to shield a contaminant free surface of the instrument which is applied to the surface of successive patients. The stack of the shields 22 including a plurality of shields, the number of which is determined based on the thickness of the material, is applied to the diaphragm 26 of the stethoscope 28 in the direction of arrow 30. With the exposed ring of adhesive 16, the stack of shields 22 is secured to the diaphragm 26 and maintained in the position illustrated in FIG. 5 with respect to the stethoscope 28. In practice, the outermost shield may become contaminated when applying the stack 22 of shields to the stethoscope 28. In this regard, prior to application of the stethoscope to a patient, the initial shield may be readily removed in the manner illustrated in FIG. 6. The initial shield 32 is grasped by the user by way of the exposed tab 24 which permits the outermost shield to be readily removed from the remaining stack 22. As noted hereinabove, the adhesive utilized in connection with the present invention is that similar to the adhesive in note pads sold by 3M Corporation under the trademark "Post-It Note". This adhesive is substantial enough to maintain the shields 10 in a stacked configuration with respect to one another, however, permits the exposed shield to be readily removed by grasping the tab 24 and peeling the exposed shield away from the remaining shields of the stack. Further, the adhesive of the initial shield contacting the instrument may be stronger than the adhesive between the remaining successive shields to aid in maintaining the stack secure with respect to the instrument as shields are removed.

As is known in the art, the stethoscope head 28 utilizes the diaphragm 26 in order to convert vibrations received from the skin of the patient into sounds which may be heard through ear pieces of the stethoscope (not shown). The stack of shields is applied to the diaphragm 26 in a manner which permits the health care provider to continue to convert these vibrations received from the skin of the patient into sounds which can be heard by the health care provider. While FIG. 3 illustrates a significant air space provided between each of the shields, this space in reality is minimal with FIG. 3 being an exaggeration of the adhesive and shield thickness. Additionally, the shields are preferably of a diameter slightly greater than that of the stethoscope diaphragm 26 to prevent the edge of the diaphragm 26 from contacting the patient.

Figure 5:
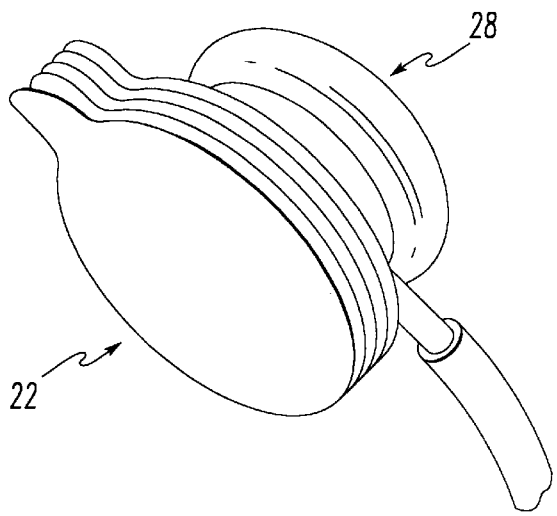
FIG. 5 is a perspective view of a plurality of shields adhered to the head of a stethoscope in accordance with the present invention.
Figure 6:
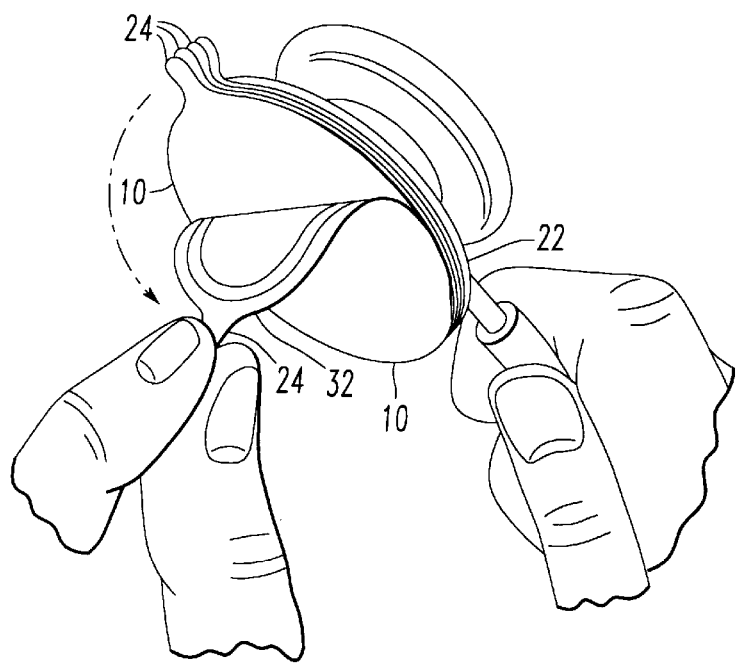
FIG. 6 is a perspective view of an outermost shield of the stack of a plurality of shields being removed from the head of a stethoscope which is to take place between uses of such stethoscope in accordance with the present invention.

As noted hereinabove, the plurality of shields forming the stack 22 are attached to the diaphragm 26 of the stethoscope 28 by a releasable adhesive so that the shield covers the entire surface of the diaphragm. This is accomplished by adhesively attaching the shield stack directly to the diaphragm 26. The thickness of the adhesive provided between the plurality of shields 10 is approximately 0.01 mils thick. Preferably, the adhesive will be no more than that necessary to hold the shields together forming the stack as well as the stack to the stethoscope itself. In such a small amount, the adhesive provides very little air space between the shields. Furthermore, because the adhesive is preferably about a periphery of the shields 10, the adhesive does not act as a barrier to the conversion of vibrations received from the skin of the patient into sounds which are detected by the health care provider. Once the stethoscope 28 having the stack 22 is formed as illustrated in FIG. 5, the stethoscope head may be applied to a patient's body. Once the examination of the this initial patient is completed, the health care provider need merely grasp the tab 24 of the exposed shield 10 and remove the shield from the stack 22 thus exposing the shield underlying the removed shield. The stethoscope can then be utilized on a subsequent patient without fear of contamination thus minimizing the transfer of microorganisms or other contaminants from one patient to the other. Additionally, the diameter of the shields may progressively decrease from the shield nearest the patient to the shield adhered to the diaphragm such that the shield contacting the patient completely covers the edges of the remaining shields in the stack as well as the edges of the stethoscope.

It should further be noted that while the foregoing discussion sets forth an adhesive being used to secure the shields to one another, the adhesion may be realized by using electrostatic forces or heat seals between the shields. This is particularly useful if the shields are of a plastic material. An adhesive may be used to secure the entire stack to the stethoscope.

As can be seen from the foregoing, the present invention provides a unit which permits the health care provider to readily perform numerous observations of patients, one after the other, while ensuring that a non-contaminated application surface is provided. The health care provider need not locate a remote stack of shields provided in the patient's room or elsewhere, but merely remove an exposed shield from a stack of shields which are already applied to the stethoscope. Once the stack has been depleted, the health care provider need merely apply a subsequent stack of shields to the stethoscope head and continue the examination of patients. Accordingly, the transfer of disease and other contaminants from patient to patient is minimized in an efficient manner in accordance with the present invention.

While the present invention has been described in reference to preferred embodiments, it will be appreciated by those skilled in the art that the invention may be practiced otherwise than as specifically described herein without departing from the spirit and scope of the invention. It is, therefore, to be understood that the spirit and scope of the invention be only limited by the appended claims.

We claim:

1. For a stethoscope having a diaphragm having a surface area for touching a body of a person, a shield unit comprising:
   a plurality of substantially planar shields stacked one upon the other, each of shields including a first surface and a second surface with said first surface of each of said shields electrostatically adhering to said second surface of an adjacent shield; and
   a first shield of said plurality of shields being adhered to said diaphragm for supporting said plurality of shields;
   wherein an exposed shield of said plurality of shields is removed after contacting the body.

2. The shield unit as defined in claim 1, wherein each of said shields includes a tab extending from a periphery thereof.

3. The shield unit as defined in claim 1, wherein an adhesive is applied to a first surface of said first shield of said plurality of shields.

4. The shield unit as defined in claim 3, further comprising a protective shield devoid of said adhesive positioned adjacent said first shield, said protective shield being removed prior to adhering said first shield to the diaphragm.

5. The shield unit as defined in claim 3, wherein said adhesive is applied to selective regions of said first surface of said first shield.

6. The shield unit as defined in claim 3, wherein said adhesive is applied adjacent a periphery of said first surface of said first shield.

7. The shield unit as defined in claim 6, wherein a central region of said first surface of said first shield is devoid of adhesive.

8. The shield unit as defined in claim 1, wherein a thickness of each of said shields is in a range of 0.10 to 4.0 mils.

9. The shield unit as defined in claim 1, wherein said shield is formed of a material which is not readily permeable by at least one of liquids and microbes.

10. The shield unit as defined in claim 1, wherein a diameter of each shield successively decreases from an outermost shield to an innermost shield of the shield unit.

11. A method for preventing contamination of an instrument comprising the steps of:
    applying a plurality of substantially planar shields stacked one upon the other to said surface of the instrument, each of said shields including a first surface and a second surface such that adjacent shields adhere to one another with said first surface of each of said shields adhering to said second surface of an adjacent shield and said first surface of a first shield in said stack adjacent the surface is adhered to the surface; and
    removing an outermost shield of said stack after said instrument has been used.

12. The method as defined in claim 11, wherein the instrument is a stethoscope and the surface is a diaphragm of the stethoscope.

13. The method as defined in claim 11, wherein each of said shields are of a dimension which covers an entire contacting surface of the diaphragm.

14. The method as defined in claim 11, wherein each of said shields includes a tab extending from a periphery thereto.

15. The shield unit as defined in claim 11, wherein an adhesive is applied to said first surface of each of said shields.

16. The method as defined in claim 15, further comprising the step of removing a protective shield from said shield to be adhered to the surface of the instrument prior to applying said plurality of shields to the surface of the instrument.

17. The method as defined in claim 15, wherein said adhesive is applied to selective regions of said first surface.

18. The shield unit as defined in claim 17, wherein said adhesive is applied adjacent a periphery of said first surface.

19. The shield unit as defined in claim 18, wherein a central region of said first surface is devoid of adhesive.

20. The shield unit as defined in claim 11, wherein a thickness of each of said shields is in a range of 0.10 to 4.0 mils.

21. The shield unit as defined in claim 11, wherein said shield is formed of a material which is not readily permeable by at least one of liquid and microbes.

22. The shield unit as defined in claim 11, wherein said first surface of each of said shields is electrostatically adhered to said second surface of said adjacent shield.

23. The shield unit as defined in claim 11, wherein said first surface of each of said shields is heat sealed to said second surface of said adjacent shield.

24. The shield unit as defined in claim 11, wherein a diameter of each shield successively decreases from an outermost shield to an innermost shield of shield unit.

25. A shield unit for application to a contact surface of an instrument comprising:

a plurality of substantially planar shields stacked one upon the other, each of shields including a first surface and a second surface such that adjacent shields adhere to one another with said first surface of each of said shields electrostatically adhering to said second surface of an adjacent shield; and a first shield of said plurality of shields being adhered to said diaphragm for supporting said plurality of shields;

wherein an exposed shield of said plurality of shields is removed after contacting the body.

26. The shield unit as defined in claim 25, wherein an adhesive is applied to a first surface of said first of shield said plurality of shields.

27. The shield unit as defined in claim in claim 26, wherein said adhesive is applied to selective regions of said first surface of said first shield.

28. The shield unit as defined in claim 25, wherein said adhesive is applied adjacent a periphery of said first surface of said first shield.

29. The shield unit as defined in claim 28, wherein a central region of said first surface of said first shield is devoid of adhesive.

30. The shield unit as defined in claim 25, wherein a thickness of each of said shields is in a range of 0.10 to 4.0 mils.

31. The shield unit as defined in claim 25, wherein said shield is formed of a material which is not readily permeable by at least one of liquid and microbes.

32. The shield unit as defined in claim 25, wherein a diameter of each shield successively decreases from an outermost shield to an innermost shield of shield unit.

33. For a stethoscope having a diaphragm having a surface area for touching a body of a person, a shield unit comprising:

a plurality of substantially planar shields stacked one upon the other, each of shields including a first surface and a second surface with said first surface of each of said shields being heat sealed to said second surface of said adjacent shield; and a first shield of said plurality of shields being adhered to said diaphragm for supporting said plurality of shields;

wherein an exposed shield of said plurality of shields is removed after contacting the body.

34. A shield unit for application to a contact surface of an instrument comprising:

a plurality of substantially planar shields stacked one upon the other, each of shields including a first surface and a second surface such that adjacent shields adhere to one another with said first surface of each of said shields being heat sealed to said second surface of said adjacent shield; and a first shield of said plurality of shields being adhered to said diaphragm for supporting said plurality of shields;

wherein an exposed shield of said plurality of shields is removed after contacting the body.

* * * * *